US008278355B2

(12) United States Patent
Puil et al.

(10) Patent No.: US 8,278,355 B2
(45) Date of Patent: Oct. 2, 2012

(54) ISOVALINE FOR TREATMENT OF PAIN

(75) Inventors: Ernest Puil, Vancouver (CA); Bernard Ansel MacLeod, Vancouver (CA); Thomas Michael Stokes, Coquitlam (CA); Wei Liu, Coquitlam (CA)

(73) Assignee: Therexcell Pharma Inc., Vancouver BC (CA)

( * ) Notice: Subject to any disclaimer, the term of this patent is extended or adjusted under 35 U.S.C. 154(b) by 352 days.

(21) Appl. No.: 12/441,054

(22) PCT Filed: Sep. 12, 2007

(86) PCT No.: PCT/CA2007/001625
§ 371 (c)(1),
(2), (4) Date: Jan. 12, 2010

(87) PCT Pub. No.: WO2008/031221
PCT Pub. Date: Mar. 20, 2008

(65) Prior Publication Data
US 2010/0137438 A1 Jun. 3, 2010

Related U.S. Application Data

(60) Provisional application No. 60/843,765, filed on Sep. 12, 2006.

(51) Int. Cl.
  A01N 37/12 (2006.01)
  A01N 43/02 (2006.01)
  A01N 31/38 (2006.01)
  A01N 43/28 (2006.01)
(52) U.S. Cl. ......... 514/561; 514/431; 514/430; 514/432
(58) Field of Classification Search .................... 514/561
  See application file for complete search history.

(56) References Cited

U.S. PATENT DOCUMENTS

(56) References Cited

| 5,626,831 | A | * | 5/1997 | Van Moerkerken | 424/9.2 |
| 5,726,200 | A | | 3/1998 | Horwell et al. | |
| 5,897,891 | A | | 4/1999 | Godfrey et al. | |
| 6,106,864 | A | | 8/2000 | Dolan et al. | |
| 6,136,294 | A | | 10/2000 | Adjei et al. | |
| 2003/0229145 | A1 | | 12/2003 | Chizh et al. | |
| 2004/0082543 | A1 | | 4/2004 | Cheung | |
| 2006/0079492 | A1 | * | 4/2006 | Ahlem et al. | 514/178 |

FOREIGN PATENT DOCUMENTS

| CA | 2424089 | 3/2003 |
| EP | 1199067 | 4/2002 |
| WO | WO 91/11172 | 8/1991 |
| WO | WO 99/31075 | 6/1999 |
| WO | WO 00/35298 | 6/2000 |
| WO | WO2005/058957 | 6/2005 |
| WO | WO 2006/069293 | 6/2006 |
| WO | WO2006/114707 | 11/2006 |

OTHER PUBLICATIONS

International Search Report fo PCT/CA2007/001625 completed Oct. 25, 2007.
Beyer, Carlos, et al., "Prevention of the Convulsant and Hyperalgesic Action of Strychnine by Intrathecal Glycine and Related Amino Acids", 1998, *Pharmcology Biochemistry & Behavior*, vol. 29, pp. 73-78.
Hylden, Janice L. K., et al., "Intrathecal Substance P Elicits a Caudally-Directed Biting and Scratching Behavior in Mice", 1981, *Brain Research*, vol. 217, pp. 212-215.
Kolesnikov, Yuri, et al., "Evaluation of the Tail Formalin Test in Mice as a New Model to Assess Local Analgesic Effects", 2004, *Brain Research*, vol. 1029, pp. 217-223.
Manner, T., et al., "The Antinociceptive Effects of Branched-Chain Amino Acids: Evidence for Their Ability to Potentiate Morphine Analgesia", 1996, *Pharmcology Biochemistry & Behavior*, vol. 53, No. 2, pp. 449-454.
Nebel, K., et al., "Stereoselective Synthesis of Isovaline (IVA) and IVA-Containing Dipeptides for use in Peptide Synthesis", 1988, *Tetrahedron*, vol. 44, No. 15, pp. 4793-4796.
Reijneveld, Jaap C., et al., "A Simple Mouse Model for Leptomeningeal Metastases and Repeated Intrathecal Therapy", 1999, *Journal of Neuro-Oncology*, vol. 42, pp. 137-142.
Skeie, Bjorn, M.D., et al., "Branch-Chain Amino Acids: Their Metabolism and Clinical Utility", 1990, *Critical Care Medicine*, vol. 18, No. 5, pp. 549-571.
Vaupel, D. B., et al., "Phencyclidine Analogs and Precursors: Rotarod and Lethal Dose Studies in the Mouse", 1984, *The Journal of Pharmacology and Experimental Therapeutics*, vol. 230, No. 1, pp. 20-27.
Abbott et al., "The formalin test: scoring properties of the first and second phases of the pain response in rats," *Pain*, 1995; 60;91-102.
Gadotti et al., "Contribution of spinal glutamatergic receptors to the antinociception caused by agmatine in mice," *Brain Research*, 2006;1093: 116-122.

Kim et al., "Activation of brainstem metabotropic glutamate receptors inhibits spinal nociception in adult rats," *Pharmacology, Biochemistry, and Behavior*, 2002; 73: 429-437.
Rao et al., "Neuropharmacological characterization of 1-aminocyclopropane-1-caroxylate and 1-aminocyclobutane-1-carboxylate, ligands of the N-methyl-D-aspartate-associated glycine receptor," *Neuropharmacology*, 1990; 29: 305-309.

(Continued)

Primary Examiner — Sreeni Padmanabhan
Assistant Examiner — Timothy E Betton
(74) Attorney, Agent, or Firm — Barnes & Thornburg LLP

(57) ABSTRACT

The invention provides for the use of isovaline or a pharmaceutically acceptable salt thereof for the treatment of Pain in a mammalian subject in some preferred embodiments, the invention provides for the treatment of acute and chronic Pain syndromes where other drug therapies have limited efficacy or unacceptable toxicity in said subject.

14 Claims, 5 Drawing Sheets

OTHER PUBLICATIONS

Hood et al., "1-aminocyclobutane-1-carboxylate (ABCD): a specific antagonist of the N-methyl-D-aspartate receptor coupled glycine receptor," *European Journal of Pharmacology*, 1989; 161: 281-282.

Haleblian, "Characterization of habits and crystalline modification of solids and their pharmaceutical," *J. Pharm. Sci.*, 1975; 64(8): 1269-1288.

*Remington's Pharmaceutical Sciences*, 19th Ed. (Mack Publishing Co.) 1995. Reference available upon request.

Verma et al, "Current Status of Drug Delivery Technologies and Future Directions," *Pharmaceutical Technology On-Line*, 2001; 25(2): 1-14.

Wan et al., "Pentobarbital modulates intrinsic and GABA-receptor conductances in thalamocortical inhibition," *Neuroscience*, 2003; 121: 947-958.

* cited by examiner

Lumbar Intrathecal Injections of Compound (Ib) and (Ic

Intravenous Injections of Compound (Ia)

ISOVALINE FOR TREATMENT OF PAIN

CROSS REFERENCE TO RELATED APPLICATIONS

This application is the U.S. national phase of PCT/CA2007/001625 filed Sep. 12, 2007. PCT/CA2007/001625 claims priority to U.S. Provisional Patent Application Ser. No. 60/843,765 filed on Sep. 12, 2006.

FIELD

The invention is in the field of preparations for medical purposes, particularly therapeutics.

BACKGROUND

Pain whether acute or chronic, may result from actual damage to body tissue, for example in general medical illnesses, arthritis, cancer, neuropathies, and perioperative conditions. Pain may also be associated with medical disorders without a known cause, such as migraine and psychosomatic illness.

Acute pain usually remits on resolution of the injury. Acute pain is typically sensitive to blockade by administration of opioids, but opioids typically have a relatively short duration of action as well as undesirable side effects.

Chronic pain may be defined as pain having a duration of 3 months or more. Chronic pain may be associated with tissue damage, and may be continuous or episodic. Like postoperative pain, chronic pain may result from excessive nociceptive stimulation as in arthritis, but often originates from neuropathy or deafferentation, inflammation and psychogenesis.

Chronic pain is often refractory to specific or routine remedies, although some therapeutic agents may have mild to moderate efficacy. Even if treated with some efficacy, chronic pain may be associated with depression, insomnia, preoccupation, disablement, with the attendant economic costs to society.

Pain responses are essential for the protection of the body from further tissue injury. Pain can become pathological with exaggerated responses to nociceptive (hyperalgesia) or non-noxious sensory stimuli (allodynia). Both forms of sensitization occur at many levels of the nervous system, including primary nociceptors, dorsal and trigeminal root cell bodies, dorsal horn interneurons, spinothalamic neurons, brainstem neurons, and various forebrain neurons. Potentially, there are accordingly a very large number of targets for analgesic drugs. The targets include sodium and calcium ion channels and receptors for agents that modulate the appreciation and reaction to pain. The presynaptic and postsynaptic receptors involved in pain transmission include sites of interaction for opioids, cannabinoids, prostaglandins, serotonin (5-HT), norepinephrine, purines, nicotine, glutamate (AMPA and NMDA receptor subtypes), as well as neutral amino acids such as GABA and glycine.

Medications routinely used for acute and chronic pain therapy are derived from several pharmacologically distinct classes: opioids, nonsteroidal antiinflammatory drugs (NSAIDs), anticonvulsants and antimigraine drugs (5-HT receptor agonists and ergot derivatives). Morphine, representing a standard analgesic of reference, belongs to the opioid class of drugs that act on the central nervous system. The actions of NSAIDs and anti-migraine drugs are primarily on peripheral tissues.

Many medications belonging to the opioid and NSAID families are efficacious against acute pain caused by excessive nociceptive stimulation. There are, however, major difficulties associated with the use of these drugs. For example, the duration of most drugs in these classes is short, requiring repeated dosing. Dangerous side effects are associated with each class. Opioids, although generally much more effective analgesics than NSAIDs, produce addiction and respiratory depression, a life threatening side effect. Therapeutic use of NSAIDs is associated with significant gastrointestinal bleeding and renal damage.

Medications belonging to the antimigraine family are efficacious in the acute treatment of headache of unknown pathophysiology. However, 5-HT agonists and ergot derivatives produce highly variable analgesic responses, both among and within individual migraine patients. The large variation in the responses to these drugs and their appreciable side effects (such as nausea and vomiting) may be attributable to their complex pharmacology.

Many opioids and NSAIDs have little or no activity against chronic pain. Some opioids may relieve chronic pain of neuropathic and psychogenic origin, but generally only at doses that have unacceptable side effects.

In treating chronic pain, medical practitioners may resort to antidepressant agents, such as agents belonging to the tricyclic class (e.g., amitryptyline) to reduce neuropathic and psychogenic pain of weak or moderate intensity. Other medications such as anxiolytics, anticonvulsants (e.g., gabapentin), sodium channel blockers (e.g., lidocaine) or glucocorticoids, may also be prescribed alone or in combination with opioids and nonopioid analgesics. In addition to limited efficacy of the available analgesics, these approaches suffer from the fact that their long-term utilization is accompanied by secondary, undesirable effects. For example, utilization of opioids is associated with problems of tolerance and dependence, NSAIDs have digestive tract toxicity, and tricyclic antidepressants may produce hypotension, sedation and weight gain.

Exogenous application of biological amino acids is known to have a very wide variety of biological effects (see for example Beyer, Banes, Gomora, and Komisaruk, Pharmacology, Biochemistry & Behaviour 29: 73-78, 1988). Isovaline is known as a substituent (U.S. Pat. No. 5,726,200), subunit (WO 2005/058957), or excipient (U.S. Pat. No. 6,136,294) in various medicaments. Isovaline has for example been used in flavouring of zinc medicaments (U.S. Pat. No. 5,897,891). For these and other purposes a number of synthetic routes are available to produce isovaline, including stereo-specific synthetic approaches (see Mutter, et al., Stereoselective Synthesis Of Isovaline (IVA) And IVA-Containing Dipeptides For Use In Peptide Synthesis; Tetrahedron Letters; 1988; vol. 44, p. 4793). Isovaline (2-Amino-2-methylbutanoic acid) is represented in base form by the formula (I):

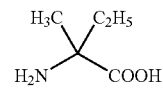

The racemate, R, and S enantiomers of isovaline are respectively referred to herein as compound (Ia), (Ib), and (Ic). The CAS Registry numbers for isovaline are: DL-isovaline [464-58-7]; L-Isovaline [595-39-1]; D-Isovaline [595-40-4]. Isovaline is not incorporated into mammalian protein. Isovaline has been found in meteoric fragments.

SUMMARY

In various aspects, the present invention relates to symptomatic treatment of pain syndromes using isovaline, including treatments for acute and chronic pain. The Examples herein accordingly illustrate the use of isovaline to achieve analgesic effects in animal models representative of acute and chronic pain. For example, Isovaline is shown to have the ability to counteract pain symptoms induced by strychnine, an antagonist of receptors for glycine-like amino acids. Isovaline may accordingly be used with alternative aspects of the invention so that it interacts therapeutically with strychnine-sensitive sites in the peripheral and central nervous systems, to produce analgesic effects.

In various aspects, the invention relates to the use of a therapeutically effective amount of an isovaline or a pharmaceutically acceptable salt thereof for the treatment of a pain in a mammalian subject, or to formulate a medicament for treating a pain in a mammalian subject. In alternative aspects, the invention provides methods for treating pain, or methods for the preparation of medications destined for preventative and/or curative treatment of pain, such as acute pain (e.g. postoperative pain), recurring episodic pain (e.g. migraine headache), and episodic or persistent chronic pain of arthritic, neuropathic, neoplastic, or psychogenic origin.

In alternative embodiments, the isovaline may be R isovaline, S isovaline or an enantiomeric mixture of R and S isovaline. Isovaline may be formulated for oral, rectal, topical, parenteral (including subcutaneous, intramuscular, intravenous and intrathecal) administration.

Patients may be selected for treatment, or treated, so that: the amount of isovaline used is effective to provide analgesia without the undesirable side effects of morphine at conventional doses; the analgesic effect of the isovaline lasts for at least 60 minutes; isovaline does not act to produce analgesia through binding to the alpha-2-delta subunit of the human calcium channel; the pain is not caused by an organic pathology for which isovaline is an effective treatment; the effective amount of isovaline is effective to have an analgesic effect in the subject but is not effective to treat any organic pathology in the subject; the amount of isovaline is effective to have an analgesic effect in the subject but is not effective to inhibit dipeptidyl peptidase IV in the subject; and, the isovaline is present in a therapeutically effective amount but not in an amount in which the isovaline is an effective adjuvant, excipient or stabilizer for a co-formulated active ingredient.

In alternative aspects, the pain to be treated may result from one or more causes, such as: a peripheral neuropathy, a central neuropathy, a traumatic abnormality, a cerebral vascular accident, postoperative pain, dental pain, direct trauma, infection, HIV infection, small pox infection, herpes infection, toxic exposure, exposure to arsenic, exposure to lead, cancer, invasive cancer, congenital defect, phantom limb pain, encephalitis, rheumatoid arthritis, fibromyalgias, spinal root lesions, spinal root impingement, back pain, multiple sclerosis, chronic pain, fibrous tissue pain, muscle pain, tendon pain, ligament pain, pain associated with diarrhea, irritable bowel syndrome, abdominal pain, chronic fatigue syndrome, and spasms.

DETAILED DESCRIPTION OF THE INVENTION

Figure 1:
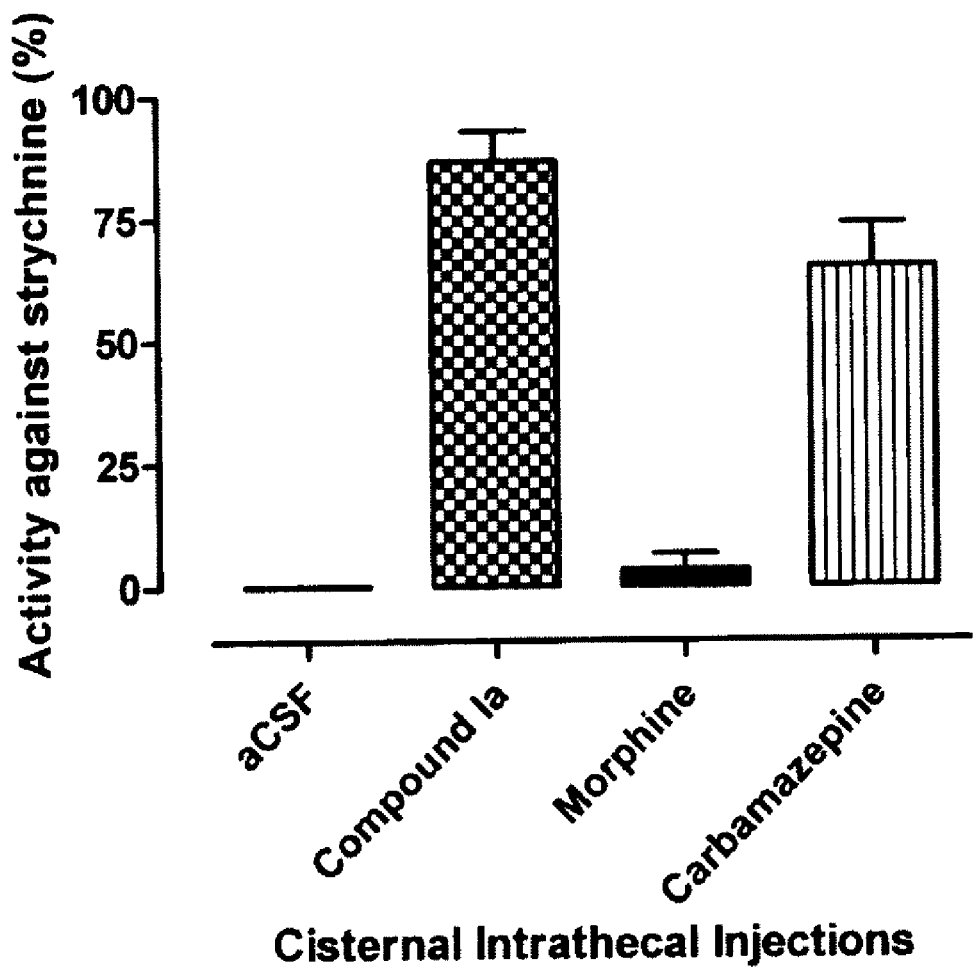
FIG. 1 shows the exemplary analgesia produced by intrathecal injection in the vicinity of the trigeminal nerve system and brainstem nuclei.

In selected aspects, the present invention pertains to the treatment of acute and chronic pain, particularly pain types that are difficult to treat with existing drugs, or are problematic due to toxic limitations. The types of pain to be treated may be broadly characterized as unpleasant sensory and emotional experiences associated with actual or potential tissue damage, and may be defined in terms of such damage. Acute pain amenable to treatments of the invention includes pain that comes on quickly but lasts a relatively short time. Perioperative pain is, for example, an acute type of pain associated with surgery. This type of pain includes responses during surgery, the immediate postoperative period (2-4 hours), and recovery period (up to 1 week). Neuropathic pain amenable to treatments of the invention encompasses an ensemble of chronic pain syndromes that originate from one or more lesions and/or dysfunctions in the central or peripheral nervous systems. Allodynia and hyperalgesia are characteristics of such neuropathic pain. Allodynia is defined as pain that results from a stimulus that ordinarily does not elicit a painful response. Hyperalgesia represents an increased sensitivity to a normally painful stimulus. These characteristics can produce a sensitization of peripheral and central somatosensory processing. Chronic neuropathic pain for treatment in accordance with the invention, such as pain that follows soft-tissue, bone, or nerve injury, may last longer and have greater severity than would have expected for the original tissue damage.

In one aspect, the invention involves the treatment of pain that is disproportionate to the causative lesion. Such pain may represent an interaction of psychic and pathological factors, and may not have apparent anatomical support or an objective lesion. For example, phantom pain is initially organic in origin but persists after disappearance of the causative lesion. Phantom pain is deeply felt as an organic sensation in a body part that was amputated. This pain may change its location in the body, and may have different manifestations and diverse or erratic intensities.

In alternative aspects, the present invention pertains to the treatment of episodic disorders such as migraine headache, and other pain syndromes which are severe and deeply felt, stabbing or lancing, insidious and dull, pressure-like with a sensation of distension, or intense and deeply felt as if produced by a sharp boring instrument.

The terms "analgesic medication", "analgesic effect" or "analgesia", mean drugs, or the effects of drugs, that reduce or suppress pain without unduly affecting other sensory modalities and conscious motor behavior. Accordingly, in some aspects of the invention, isovaline is used so as to prevent or block acute and chronic pain in animals without undue side effects.

In various aspects of the invention, the administration of isovaline may be carried out so as to produce a dose dependent reduction in the intensity of pain symptoms. The pain symptoms may for example be objectified by the measurement of different behavior and/or conscious physiological parameters such as vocalization, inordinate responses to normal sensory stimulation, etc. The analgesic effect may be maintained in as much as the circulating amounts of the analgesic compound are adjusted by dosing so as to be sufficient for exerting its analgesic activity. The analgesic effects may be reversible, as would be evident from augmenting pain intensity that tends to again reach a level near the initial level (i.e., the pain threshold before treatment).

Many types of chronic pain of neuropathic and psychogenic origin are potentially sensitive to the action of the preparations of the invention. From the features of the illustrated Examples, one can more specifically cite pain of peripheral or central neuropathies resulting from abnormalities that are traumatic in origin (e.g., cerebral vascular accident, postoperative, dental, and associated with direct trauma), infectious (e.g., encephalitis, herpes, HIV, small pox), toxic (arsenic, lead), invasive (cancer), and congenital, or pain that is associated with phantom limb, rheumatoid arthritis, spinal root lesions or impingement (e.g. back pain), and multiple sclerosis, or other chronic pain. Pain is considered chronic when a patient has begun to suffer for a period of 3 months. Among "other chronic pain", one can cite from the features of the illustrated Examples, pain associated with fibromyalgias, a fibrous tissue provenance, muscles, tendons, ligaments and other sites, and diarrhea (notably in the case of irritable bowel syndrome), as well as abdominal and back pain. The present invention relates in particular also to the treatment of certain symptoms of chronic fatigue syndrome, characterized by a state of exhaustion or fatigue associated notably with spasms and/or muscular pain.

In one aspect, the invention involves administration (including co-administration) of therapeutic compounds or compositions, such as isovaline of Formula (I), and the corresponding salts of addition with acids or bases, so as to achieve analgesia in a subject. In various embodiments, such agents may be used therapeutically in formulations or medicaments. Accordingly, the invention provides therapeutic compositions comprising active agents, including analgesic agents that achieve an analgesic effect in a subject, together with pharmacologically acceptable excipients or carriers.

An effective amount of an agent of the invention will generally be a therapeutically effective amount. A "therapeutically effective amount" generally refers to an amount effective, at dosages and for periods of time necessary to achieve the desired therapeutic result, such as analgesia. A therapeutically effective amount of a compound may vary according to factors such as the route of administration, disease state, age, sex, and weight of the individual, sensitivity of the patient, all of which relate to the ability of the compound to elicit a desired response in the individual. Dosage regimens may be adjusted to provide the optimum therapeutic response. A therapeutically effective amount is also one in which any toxic or detrimental effects of the compound are outweighed by the therapeutically beneficial effects.

In particular embodiments, for any particular subject, specific dosage regimens should be adjusted over time according to the individual need and the professional judgement of the person administering or supervising the administration of the compositions.

A "pharmaceutically acceptable carrier" or "excipient" includes any and all solvents, dispersion media, coatings, antibacterial and antifungal agents, isotonic and absorption delaying agents, and the like that are physiologically compatible. In some embodiments, the carrier is suitable for parenteral or intrathecal administration. Alternatively, the carrier can be suitable for intravenous, intraperitoneal, intramuscular, sublingual or oral administration. Pharmaceutically acceptable carriers include sterile aqueous solutions or dispersions and sterile powders for the extemporaneous preparation of sterile injectable solutions or dispersion. Supplementary active compounds can also be incorporated into compositions of the invention.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, active agents of the invention may be administered in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

Sterile injectable solutions can be prepared by incorporating the active agent in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

In accordance with another aspect of the invention, therapeutic agents of the present invention, such as isovaline and salts thereof, may be provided in containers having labels that provide instructions for use of, or to indicate the contents as, analgesics, such as compounds to treat, suppress or ameliorate pain, or for treating diseases or disorders listed herein as associated with pain.

Use of the present invention to treat or prevent a disease condition as disclosed herein, including prevention of further disease progression, may be conducted in subjects diagnosed or otherwise determined to be afflicted or at risk of developing the condition, i.e. pain.

Routes of administration for agents of the invention may vary, and may for example include intradermal, transdermal, parenteral, intravenous, intramuscular, intranasal, subcutaneous, regional, percutaneous, intratracheal, intraperitoneal, intraarterial, intravesical, intratumoral, intrathecal, inhalation, perfusion, lavage, direct injection, and oral administration and formulation. Accordingly, compositions of the invention may be adapted to be administrable nasally, sublingually, rectally, transcutaneously, parenterally, intrathecally or subarachnoidally. Methods of the present invention may be used prophylactically, for example preoperatively.

Continuous administration of agents of the invention may be applied, where appropriate. Generally, the dose of the therapeutic agent via continuous perfusion will be equivalent to that given by a single or multiple injections, adjusted over a period of time during which the perfusion occurs.

Treatments of the invention may include various "unit doses." A unit dose is defined as containing a predetermined-quantity of the therapeutic composition. A unit dose need not be administered as a single injection but may comprise continuous infusion over a set period of time.

Although various embodiments of the invention are disclosed herein, including in the following Examples, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to the present invention. Any priority document(s) and all publications, including but not limited to patents and patent applications, cited in this specification are incorporated herein by reference as if each individual publication were specifically and individually indicated to be incorporated by reference herein and as though fully set forth herein. The invention includes all embodiments and variations substantially as hereinbefore described and with reference to the Examples and drawings.

EXAMPLES

These Examples illustrate the analgesic efficacy of isovaline in animal models representative of acute and chronic pain. Analgesic activity of compounds (Ia), (Ib), and (Ic) is illustrated in models involving trigeminal and lumbar pain, and pain of formalin injection in the mouse foot. The Examples illustrate the therapeutic effect, including a lack of apparent central nervous system toxicity, conferred by the administration of the compounds of the invention. In particular, the Examples substantiate the following aspects of the invention.

(i) The racemate (Ia) of isovaline and its stereoisomers (Ib and Ic) are endowed with analgesic activity against acute and chronic pain.

(ii) The analgesic actions of compound (Ia), (Ib), and (Ic) were rapid in onset and blocked the acute generation of pain responses.

(iii) The duration of the analgesic responses to compound (Ia), (Ib), and (Ic) was long and potentially curative in protracted pain.

(iv) At effective doses, compound (Ia) and stereoisomers (Ib) and (Ic) have analgesic actions that are not limited by secondary side effects.

(v) The long-lasting blockade of hyperalgesia or allodynia produced by systemic administration of compound (Ia), (Ib), and (Ic) is unique, and unknown for currently available analgesics used in treatment of acute and chronic pain.

Example 1

Trigeminal Intrathecal Administration of Compound (Ia), (Ib), and (Ic) Blocked Strychnine-Induced Allodynia Strychnine when administered alone to the intact rodent mimics the allodynia of chronic pain resulting from damage to inhibitory amino acid functions in the central nervous system.

In the present example, injections into the cisterna magna of the mouse were performed as described by Reijneveld, Taphoorn, and Voerst (Journal of Neurooncology 42: 137-142, 1999). Each series of experiments consisted of 6 to 9 pairs of mice. The total volume used for injection in all experiments was 5 microliters of artificial cerebrospinal fluid (aCSF). Strychnine at 200 micromolar in 5 microliters of aCSF was injected alone and in combination with compound (Ia), (Ib), or (Ic). In each session, two mice were injected with the strychnine solution within one minute of each other. Hence the control mouse received strychnine at 200 micromolar in aCSF whereas the treated mouse received strychnine at 200 micromolar and compound (Ia), (Ib), or (Ic) at 4 millimolar. The mice were placed in a container designed such that they could be simultaneously observed, but would be unaware of the other. The presence of flinching, scratching or vocalization in response to touching with a fine hair was noted every 2 minutes. A continuous video recording was made of all responses. A blinded observer decided which animal had the greatest response to stimuli. A Wilcoxon signed rank test was used to determine the statistical significance of the results.

Results

Figure 2:
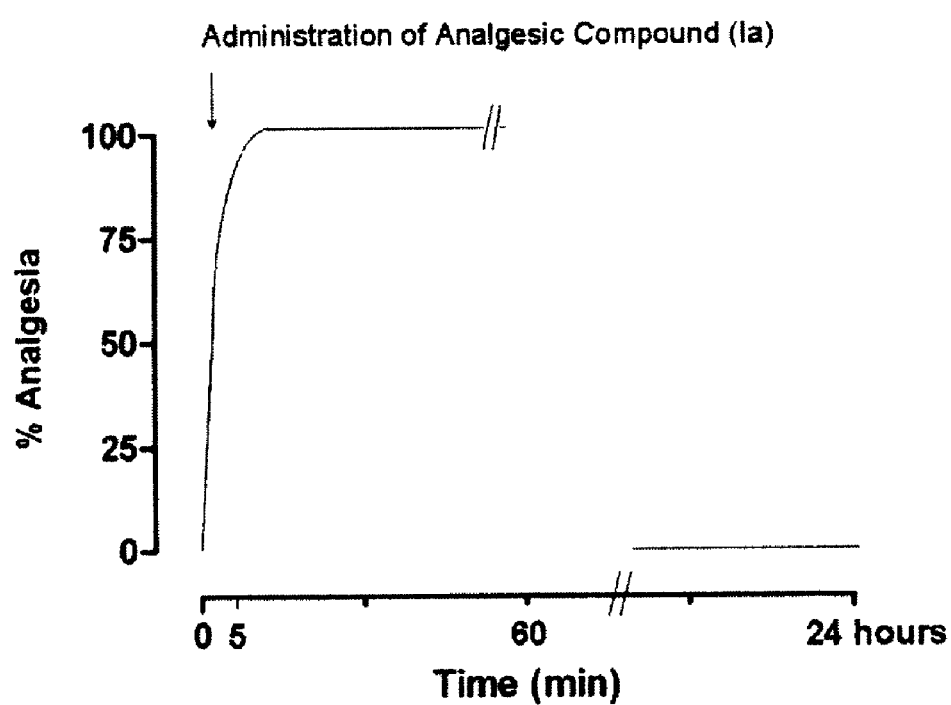
FIG. 2 shows the exemplary time course of the analgesia produced by intrathecal injection.

A positive response (vocalization, flinching, and scratching) representing hyperalgesia or allodynia occurred on exposure to a jet of air to the skin or when the observer touched skin that corresponded to the somatic distribution of the trigeminal nerve (i.e., innervation by the trigeminal nerve). FIG. 1 shows that administration of compound (Ia) at 4 millimolar resulted a great reduction and a total blockade of hyperalgesia or allodynia in treated animals. The same effects were obtained with compound (Ib) and (Ic) and were significant at a level of $p<0.01$. The behavior of mice treated with compound (Ia), (Ib), or (Ic) and strychnine was identical to the mice which received the aCSF control injection without strychnine. The treated animals showed no side effects such as sedation, movement disorders, or abnormal behavior. The analgesic effects of compound (Ia), (Ib), or (Ic) lasted at least 60 minutes (FIG. 2).

FIG. 1 also shows that the responses to intracisternal injections of the reference analgesic, morphine (1 mg/kg body weight), were poor or absent. The effects of morphine in this trigeminal animal model correlate with the poor responses to morphine and other opioids observed in human chronic pain. In the same model and FIG. 1, there was an analgesic effect of carbamazepine epoxide (30 mg/kg body weight), the principal active metabolite of the main drug used to treat human trigeminal neuralgia. The analgesia produced by the carbamazepine epoxide is further evidence for the validity of the animal model for trigeminal pain, used to demonstrate the analgesic effect of compound (Ia), (Ib), and (Ic).

Example 2

Lumbar Intrathecal Administration of Compound (Ia) Blocked Strychnine-Induced Allodynia Injections into the 6th lumbar intrathecal space were performed according to the method of Hylden and Wilcox (Brain Research 217: 212-215, 1981). The total volume used for injection in all experiments was 5 microliters of artificial cerebrospinal fluid (aCSF). In mice anesthetized with isoflurane, strychnine at 200 micromolar in 5 microliters of aCSF was injected either alone or in combination with compound (Ia) at concentrations of 4 to 8 millimolar in a total volume of 5 microliters of aCSF. In each experiment 2 mice were injected with 5 microliters of solution within one minute of each other. One of the mice received strychnine 200 micromolar in aCSF (control) and the other received the same volume with strychnine 200 micromolar in combination with the test compound (Ia). The mice were placed in a container designed such that they were unaware of the other, but could be simultaneously observed. The presence of flinching, scratching or vocalization in response to touching with a fine hair was noted every two minutes. Responses limited to lumbar segments 5 and 6, as well as originating from more caudal nerve distribution were considered as positive. A continuous video recording was made of all responses. Each experiment consisted of 6 to 9 pairs of mice. The blinded observer decided which animal had the greatest response to stimuli. A Wilcoxon signed rank test was used to determine the statistical significance of the results.

Results

Figure 3:
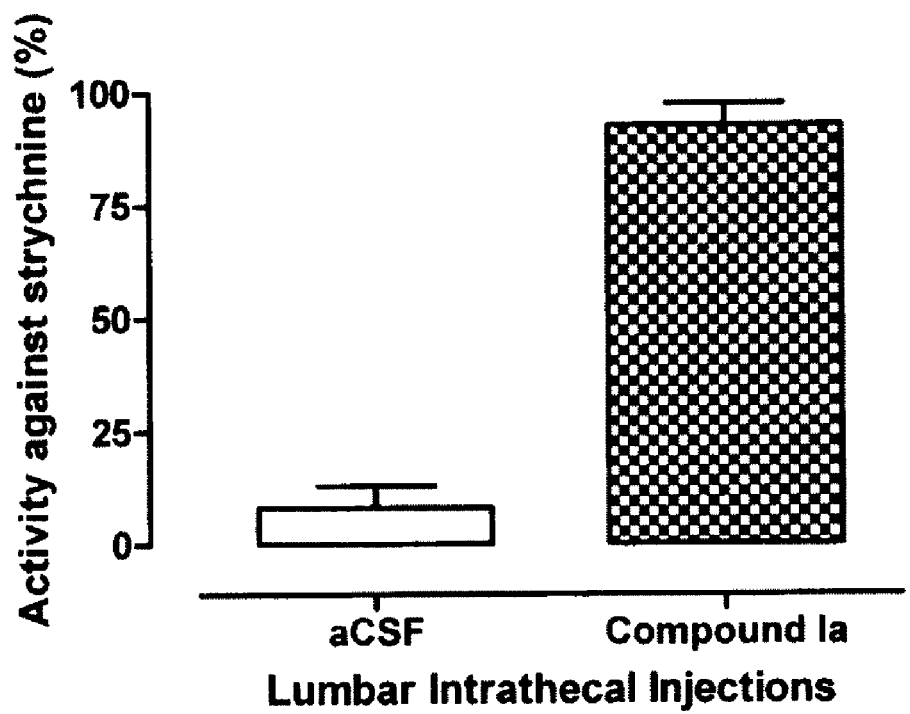
FIG. 3 shows the exemplary analgesia produced by intrathecal injection in the lumbar region of the spinal cord.

The response to light touch was confined to the nerve distribution of the 5th to 6th lumbar and more caudal segments. The sole administration of 25 microliters compound (Ia) at 10 millimolar did not produce a significant result. Without concomitant strychnine injection, the behavior of mice treated with compound (Ia) was identical to those mice that received aCSF control injection. FIG. 3 shows that a 5 microliter injection of strychnine at 200 micromolar plus compound (Ia) at 8 millimolar resulted in identifying the presence of compound (Ia) by the blinded observer in 6 out of 6 pairs of mice. The treated animals showed no sedation, movement disorders, or abnormal behaviour. The blockade of strychnine-induced effects was significant at a level of $p<0.01$. The effect of compound Ia, as in the previous experiments (cf. FIG. 2) was noted to last at least 60 minutes. This abolition or reduction of hyperalgesia or allodynia represented an analgesic effect, without sedation, motor impairment, sensory impairment, or tranquillization.

Example 3

Lumbar Intrathecal Compound (Ib) and (Ic) Reduced Peripheral Acute and Chronic Pain The effects of compound (Ib) and (Ic) were determined in the acute and chronic peripheral pain model according to Kolesnikov, Cristea, Oksman, Torosjan, and Wilson (Brain Research 17: 217-223, 2004). Use of this model involves pre-treatment with the test compound and injection of formalin (5% in 20 microliters) into the right hindpaw of mice. Groups of mice (n=10) were injected intrathecally into the lumbar segment with compound (Ib) or (Ic) at 250 micromolar in 5 microliters, at 5 minutes prior to subcutaneous formalin injection into the right hindpaw. The mice were monitored for 40 min for licking activity and assessed according to the method of Abbott, Franklin, and Westbrook (Pain 60: 91-102, 1995). The cumulative licking activity in seconds per 5 minute bin was plotted, comparing the results obtained with aCSF control and compound (Ib) or (Ic).

Results

Figure 4:
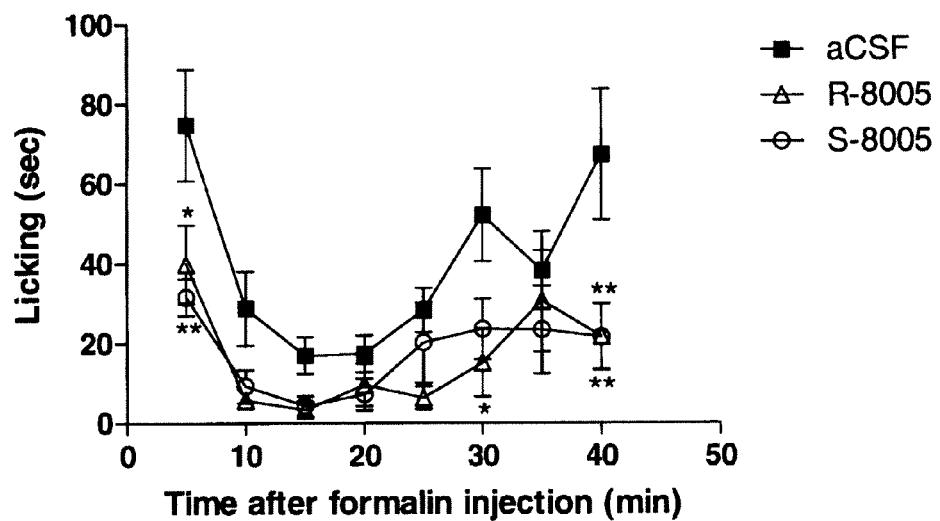
FIG. 4 shows the analgesia produced by intrathecal injection against formalin foot injection licking time.

The cumulative paw licking was significantly reduced by compound (Ib) or (Ic) with p-value<0.001. FIG. 4 shows that the means (±SEM) of both the early (reflecting acute pain) and late (reflecting chronic pain) phases were significantly reduced by compound Ib and Ic (*$p<0.05$, **$p<0.01$ compared with the control group).

Example 4

Intravenous Compound (Ia) Reduced Peripherally Induced Chronic Pain

Groups of mice (n=10) were injected intravenously with a dose of 500 mg/kg of compound (Ia) at 10 minutes prior to subcutaneous formalin injection into the right hindpaw. After the injection of formalin (5% in 20 microliters), the animals were monitored for 40 min for licking activity. The cumulative licking activity in seconds per 5 minute bin was plotted, comparing the results obtained with 0.9% NaCl control and compound (Ia).

Results

Figure 5:
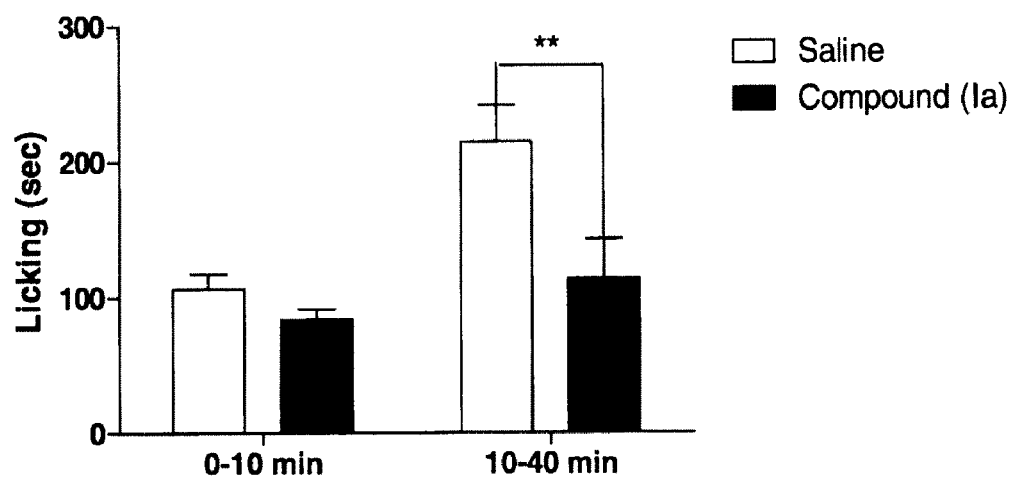
FIG. 5 shows the analgesia produced by intravenous injection against formalin foot injection licking time.

The cumulative paw licking at 10 to 40 minutes after formalin injection was compared on administration of either saline or compound (Ia). FIG. 5 shows that compound (Ia) significantly reduced the mean (±SEM) of the late phase reflecting chronic pain (**$p<0.001$ compared with the control group).

Overall, the results of experiments showed that compounds (Ia), (Ib), and (Ic) produced analgesia against trigeminal hyperalgesia or allodynia to a much greater degree than the tested reference opioid, morphine, and surpassed the analgesia produced by carbamazepine, the current mainstay drug for treatment of trigeminal neuralgia. Furthermore, compound (Ia), (Ib) and (Ic) administered to the lumbar cord was active against acute and chronic pain induced peripherally. Intravenous administration of compound (Ib) and (Ic) was effective in producing analgesia in peripherally induced pain, demonstrating that compound of Formula I crosses the blood-brain-barrier.

Example 5

Intravenous Administration of Compound (Ib) and (Ic) Did not Produce Central Toxicity in Rotarod Test Changes in central nervous system behavior viewed as ataxia were measured using the rotarod procedure in mice, described by Vaupel, McConn, and Cone (Journal of Pharmacology & Experimental Therapeutics, 230: 20-27, 1984). A 27-mm diameter rod was rotated at 5 rpm. At least 1 day before testing, mice were trained in three sessions on the rod for two consecutive 5 minute trials, separated by a 5 minute rest period. During the tests, each trial on the rotarod was limited to a 120 seconds maximum. For all experiments two control trials obtained 6 minutes apart preceded the injection (500 mg/kg, 3 ml/kg) of compound (Ib) or (Ic) into the tail vein. Each mouse was then given 2 trials, with 6 minutes between trials after the injection.

Results

The data were analyzed as means±SEM of 10 mice in each group, and examined by analysis of variance (ANOVA) for multiple comparisons with the single control group. Level of significance was set to 5% ($p<0.05$). The mice did not show significant differences between control saline and either compound (Ib) or (Ic), as well as between pre- and post-injection of either saline or compound (Ib) or (Ic). Therefore there was no evidence from this test that the compound of Formula (I) produced central nervous system toxicity, such as ataxia or other disturbances in conscious behavior.

Overall in addition to the experiments of Example 5, there was no observed behavioral toxicity of compound (Ia), (Ib) and (Ic) in the animals studied and described in this invention.

What is claimed is:

1. A method of treating a pain in a mammalian subject in need thereof, comprising administering to the subject an amount of an isovaline or a pharmaceutically acceptable salt thereof wherein the isovaline is the sole active agent.

2. The method according to claim 1, wherein the isovaline is R isovaline.

3. The method according to claim 1, wherein the isovaline is S isovaline.

4. The method according to claim 1, wherein the isovaline comprises R and S isovaline.

5. The method according to claim 1, wherein the subject is a human.

6. The method according to claim 1, wherein the isovaline is administered parenterally.

7. The method according to claim 1, wherein the isovaline is administered intrathecally.

8. The method according to claim 1, wherein the pain is a neuropathic pain.

9. The method according to claim 1, wherein the pain is not associated with a diabetic neuropathy.

10. The method according to claim 1, wherein the pain is not caused by an organic pathology.

11. The method according to claim 1, wherein the effective amount of isovaline has an analgesic effect in the subject but is not effective to treat pain caused by an organic pathology in the subject.

12. The method according to claim 1, wherein the effective amount of isovaline has an analgesic effect in the subject but is not effective to inhibit dipeptidyl peptidase IV in the subject.

13. The method according to claim 1, wherein the pain results from one or more causes selected from the group consisting of: a peripheral neuropathy, a central neuropathy, a traumatic abnormality, a cerebral vascular accident, postoperative pain, dental pain, direct trauma, infection, HIV infection, small pox infection, herpes infection, toxic exposure, exposure to arsenic, exposure to lead, cancer, invasive cancer, congenital defect, phantom limb pain, encephalitis, rheumatoid arthritis, fibromyalgias, spinal root lesions, spinal root impingment, back pain, multiple sclerosis, chronic pain, fibrous tissue pain, muscle pain, tendon pain, ligament pain, pain associated with diarrhea, irritable bowel syndrome, abdominal pain, chronic fatigue syndrome, and spasms.

14. The method according to claim 1, wherein the subject has been diagnosed as being refractory to effective treatment with at least one analgesic other than isovaline.

\* \* \* \* \*